(12) United States Patent
Xie

(10) Patent No.: US 7,944,566 B2
(45) Date of Patent: May 17, 2011

(54) SINGLE FIBER ENDOSCOPIC FULL-FIELD OPTICAL COHERENCE TOMOGRAPHY (OCT) IMAGING PROBE

(75) Inventor: Huikai Xie, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 955 days.

(21) Appl. No.: 11/814,112

(22) PCT Filed: Feb. 3, 2006

(86) PCT No.: PCT/US2006/004469
§ 371 (c)(1),
(2), (4) Date: Jul. 17, 2007

(87) PCT Pub. No.: WO2006/084279
PCT Pub. Date: Aug. 10, 2006

(65) Prior Publication Data
US 2010/0157308 A1 Jun. 24, 2010

Related U.S. Application Data

(60) Provisional application No. 60/650,188, filed on Feb. 4, 2005.

(51) Int. Cl.
*G01B 9/02* (2006.01)
*G01B 11/02* (2006.01)
(52) U.S. Cl. .................. 356/479; 356/497
(58) Field of Classification Search .......... 356/479, 356/497
See application file for complete search history.

(56) References Cited

U.S. PATENT DOCUMENTS

| 7,450,244 B2 * | 11/2008 | Xie ................... 356/479 |
| 2002/0093655 A1 * | 7/2002 | Everett et al. |
| 2003/0142934 A1 * | 7/2003 | Pan et al. |
| 2004/0218877 A1 * | 11/2004 | Xie |
| 2006/0269896 A1 * | 11/2006 | Liu et al. ............ 433/29 |
| 2007/0238930 A1 * | 10/2007 | Wiklof et al. ........ 600/160 |
| 2008/0186501 A1 * | 8/2008 | Xie ................... 356/450 |

FOREIGN PATENT DOCUMENTS

WO   WO 03/073041 A  * 9/2003

OTHER PUBLICATIONS

Hitzenberger, et al., "Three-Dimensional Imaging of the Human Retina by High-Speed Optical Coherence Tomography," Optics Express 2753-2761, Oct. 20, 2003, vol. 11, No. 21.

* cited by examiner

*Primary Examiner* — Patrick J Connolly
(74) *Attorney, Agent, or Firm* — Thomas, Kayden, Horstemeyer & Risley, LLP

(57) ABSTRACT

A single fiber full-field optical coherence tomography (OCT) imaging probe (300) includes a hollow tube (301), and a single fiber (305) disposed within the tube for transmitting light received from a broadband light source to a beam splitter (350) in the tube optically coupled to the single fiber (305). The beam splitter (350) splits the light into a first and a second optical beam, wherein the first beam is optically coupled to a reference arm including a MEMS reference micromirror (335) which provides axial scanning and the second beam is optically coupled to a sample arm for probing a sample to be imaged. Both the reference arm and the sample ami are disposed in the tube. A photodetector array (315) is preferably disposed inside the tube (301) optically coupled to the beam splitter (350). The photodetector array (315) receives a reflected beam from the MEMS reference micromirror (335) and a scattered beam from the sample to form an image of the sample.

11 Claims, 7 Drawing Sheets

SINGLE FIBER ENDOSCOPIC FULL-FIELD OPTICAL COHERENCE TOMOGRAPHY (OCT) IMAGING PROBE

CROSS-REFERENCE TO RELATED APPLICATIONS

This application is the national stage entry of International Application No. PCT/US2006/004469, filed Feb. 3, 2006, which claims priority to U.S. Provisional Patent Application No. 60/650,188, filed Feb. 4, 2005.

FIELD OF THE INVENTION

The invention relates to single-fiber full field optical coherence tomography (OCT) imaging probes based on embedded MEMS mirrors.

BACKGROUND OF THE INVENTION

Optical coherence tomography (OCT), sometimes referred to as "optical biopsy", can be used to obtain high-resolution (~10 μm) cross-sectional imaging of scattering biological tissues up to 3 mm deep. OCT is based on low-coherence interferometery and fiber optic technology. The core of an OCT system is a Michelson interferometer, a simplified schematic of which is shown in FIG. 1. For a typical fiberoptic OCT imaging system, such as system 100 shown in FIG. 1, two optical fibers after the beam splitter 110 are required. A first optical fiber (fiber 1) is used for the reference arm of the interferometer, while a second optical fiber (fiber 2) is used for the sample arm of the interferometer which scans the sample 120. The reference arm is external to the probe, while the sample arm including fiber 2 and the sample arm optical components are embedded inside the imaging probe, such as within a catheter for insertion into the body cavity of a patient. For cardiovascular imaging and endoscopic imaging, slender catheters are required. Accordingly, the OCT must be constructed as a slender imaging probe.

Optical interference is detected by the photodetector 125 only when the optical path difference between the reference and sample arms is within the coherence length of the light source 130. Depth information of the sample is acquired through the axial scanning (z) of the optical delay line provided by reference mirror 135 in the reference arm. Two-dimensional (2D, i.e., x-z) cross-sectional images are obtained by a 1D (or 2D) transversely scanning mirror 140. 3D images can also be obtained if a 2D transversely x-y scanning mirror is provided.

The axial resolution is determined by the coherence length. Low coherence is obtained by using a broadband light source such as a superluminescent diode (SLD) or a femtosecond laser. The coherence length of a broadband light source is given by $0.44\bar{\lambda}^2/\Delta\lambda$, where $\bar{\lambda}$ and $\Delta\lambda$ are respectively the center wavelength and spectral bandwidth of the light source. For example, a SLD with a center wavelength of 1300 nm and a bandwidth of 90 nm has a coherence length of 8 μm. Thus, OCT imaging can achieve at least one order of magnitude higher spatial resolution compared to commonly used ultrasound imaging (~100 μm). Furthermore, study shows that more than 85% of all cancers originate in the epithelial layer which is within the penetration depth of infrared laser beams. Thus, OCT can be used for cancer diagnosis and has been applied to a wide variety of biological tissue and organ systems including eyes, skin, teeth, gastrointestinal tracts and respiratory tracts. OCT can also be used for cardiovascular imaging. Cancer and heart disease are the top two killers in U.S. and most of the developed world.

OCT provides high-resolution cross-sectional images, which is suitable for early cancer diagnostics and plaque detection in coronary arteries. Conventional OCT obtains image data pixel by pixel. Each pixel corresponds to an axial scan and a lateral scan. The light beam focus size thus determines the image resolution. Full-field OCT systems have been reported to overcome some of these problems. In full-field OCT systems, a two-dimensional (2D) image is obtained for each axial scan without any lateral scan. As a result, images can be generated much faster in comparison to conventional OCT. Furthermore, high resolution can be obtained by using a large array of photodetectors, not limited by the light beam spot size. However, current full-field OCT systems require the Michelson interferometer formed in free space to provide spatial and phase correlations. Thus they are bulky and are accordingly limited biopsy samples, or for external use.

SUMMARY

A single fiber full-field optical coherence tomography (OCT) imaging probe includes a hollow tube, and a single fiber disposed within the tube for transmitting light received from a broadband light source to a beam splitter in the tube optically coupled to the single fiber. The beam splitter splits the light into a first and a second optical beam, wherein the first beam is optically coupled to a reference arm including a MEMS reference micromirror which provides axial scanning and the second beam is optically coupled to a sample arm for probing a sample to be imaged. Both the reference arm and the sample arm are disposed in the tube. A photodetector array is preferably disposed inside the tube optically coupled to the beam splitter. The photodetector array receives a reflected beam from the MEMS reference micromirror and a scattered beam from the sample to form an image of the sample.

The MEMS reference micromirror comprises can be a vertical displacement (LVD) MEMS micromirror. The LVD micromirror can comprise an electrothermal bimorph actuator, a rigid frame and a mirror plate, wherein the LVD micromirror generates vertical motion. The LVD micromirror can include an integrated accelerometer on the same die. The accelerometer can be a three-axis accelerometer. The probe can include a wireless transceiver disposed inside the tube communicably coupled to the photodetector, wherein the transceiver transmits image data obtained from the photodetector over the air.

The probe can further comprises a mirror disposed in the sample arm, wherein the mirror directs the second beam to a side of the tube for side-view scanning of the sample. The mirror is preferably a MEMS scanning mirror, but can also be a fixed mirror.

An optical coherence tomographic (OCT) probe-based imaging system for viewing a sample comprises the probe recited in claim 2, and a control module including at least one broadband light source for coupling the broadband light into the single fiber, and signal processing and synchronization electronics for coordinating, detecting and processing optical interference resulting from a scattered beam from the sample and a reflected beam from the reference arm both received via the single fiber. The system can further comprise a wireless transceiver disposed inside the tube communicably coupled to the photodetector, wherein the transceiver transmits image data over the air obtained from the photodetector.

BRIEF DESCRIPTION OF THE DRAWINGS

There are several embodiments shown in the drawings which are presently preferred, it being understood, however, that the invention can be embodied in other forms without departing from the spirit or essential attributes thereof.

In FIG. 4, an additional beamsplitter is inserted to enable the placement of the photodetector array and transceiver in a less crowded region.

DETAILED DESCRIPTION OF THE INVENTION

Figure 1:
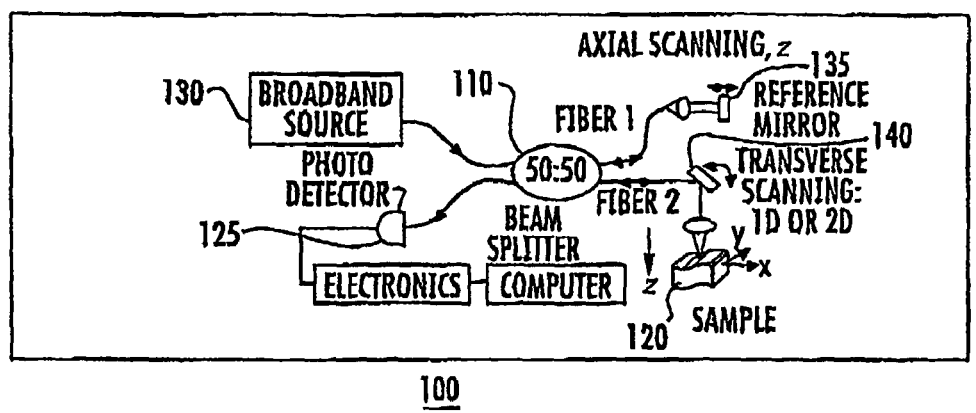
FIG. 1 shows a simplified schematic of a conventional prior art optical coherence tomography (OCT) system.

An optical coherence tomography (OCT) probe for probing a sample comprises a hollow and preferably flexible tube, and a single fiber within the tube for transmitting light received from a broadband light source to a beam splitter in the tube. The beam splitter splits light from the broadband light source into a first and a second optical beam. The first beam is directed to a reference arm and the second beam is directed to a sample arm for probing the sample to be imaged, wherein the reference arm and the sample arm are both embedded in the tube, thus permitting single optical fiber operation. A photodetector is also provided for forming an image of the sample through receipt of the reflected beam from the MEMS reference micromirror and the scattered beam from the sample. Although the photodetector can be disposed external to the probe, in a preferred embodiment the photodetector array is disposed inside the tube.

The single-fiber full field OCT imaging probe is based on MEMS (Microelectromechanical Systems) technology. MEMS devices described herein, including the MEMS micromirrors, such as the large-vertical-displacement (LVD) micromirror for axial scanning in the reference arm and MEMS scanning mirrors in the sample arm, can all be fabricated using a single conventional CMOS-MEMS processes. Significantly, MEMS devices are generally small enough (on the order of several $mm^2$) to be embedded inside an imaging probe. A CMOS accelerometer can also be integrated on the same die as the MEMS micromirrors to monitor the motion of the imaging probe in real-time.

Accordingly, OCT systems according to the invention provide fast 3D imaging with greatly reduced motion artifacts. Further simplification and performance improvement can be achieved by optionally placing a wireless transmitter within the imaging probe. The power for the embedded electronics can be provided by several power sources, including but not limited to a battery, a microwave source or a laser. Laser power is generally preferable since the same fiber can be used to deliver the broadband light source and the laser light for powering the embedded electronics as well. Alternatively, a second fiber can be used to just deliver the light for generating power.

After the beam splitter, the light travels in free space. As used herein "free-space" in this application refers to outside a waveguide, such as a fiber, but still inside the tube. Therefore, the probe can be used as a full-field OCT imaging probe by placing an imager (e.g., IR photodetector array) also inside the probe.

The invention can generally provide image scanning in at least two modes. There are two orthogonal transverse scan axes (i.e., x and y) and one axial scan axis (i.e., z, or A-scan). There are also two operating modes: cross-sectional scan and en face scan. In the cross-sectional scan mode, the axial z-scan plus one transverse y-scan generates a 2D cross-sectional image. This y-z scan is also called B-scan in ultrasound imaging. A series of B-scans along the x-axis will produce a 3D image. In the en face scanning mode, a transverse 2D x-y image frame is scanned first, followed by the axial z-scan to produce a 3D image.

As noted above, the embedded reference arm is enabled by a MEMS micromirror which provides out-of-plane movement of at least about 1 mm for axial scanning and a footprint of less than about 2~3 mm. Such a micromirror is preferably realized using a large-vertical-displacement (LVD) MEMS micromirror, such as the LVD disclosed in U.S. Pat. No. 6,940,630 (also published as Published Application No. 20040218877 on Nov. 4, 2004). The LVD is only a few-millimeters in size and moves out of plane to provide a large vertical displacement for axial scanning. In a preferred embodiment, the LVD mirror also simultaneously oscillates at high frequency to provide phase modulation. Thus, using a LVD micromirror as the reference mirror, a free-space interferometer, such as a Michelson interferometer, can be formed entirely inside the endoscopic imaging probe. An array of photodetectors can be also placed inside the imaging probe to pick up a 2D image frame at each axial scan without any lateral scans.

Figure 2:
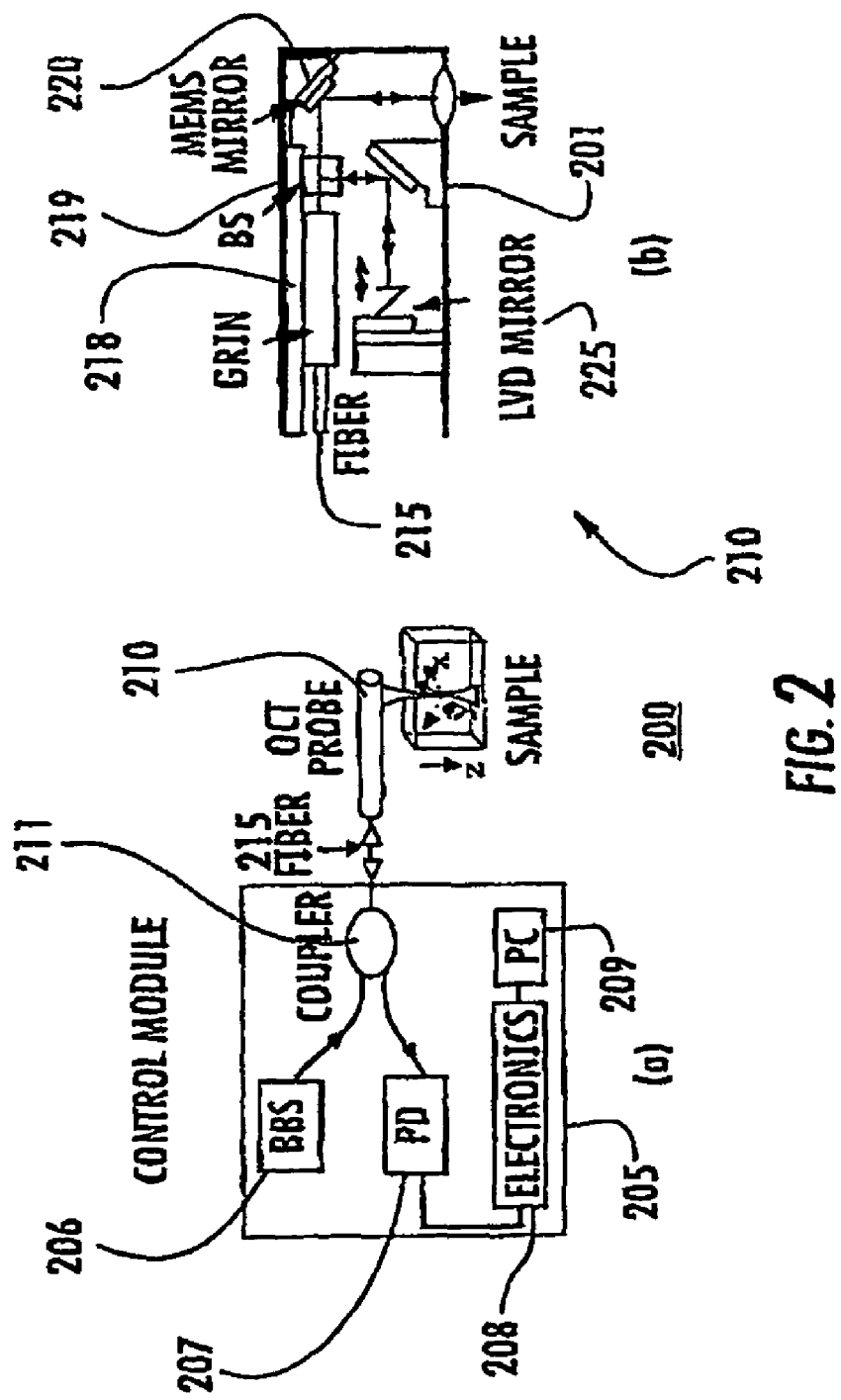
FIG. 2(a) shows a simplified schematic of a single fiber full-field OCT probe according to an embodiment of the invention.
FIG. 2(b) shows a cross sectional view of a full-field side-view endoscopic OCT imaging probe including an embedded large-vertical-displacement (LVD) micromirror as the reference mirror, according to an embodiment of the invention.

FIG. 2(a) shows a schematic of a single fiber OCT imaging probe-system 200 according to an embodiment of the invention. System 200 includes control module 205 and OCT probe 210 which are coupled to one another by fiber 215. Control module 205 includes a broadband light source (BBS) 206, photodetector (PD) 207, electronics 208 and computer (PC) 209. Electronics 208 provides coordinating, detecting and processing of optical interference resulting from a scattered beam from the sample and a reflected beam from the reference arm Broadband light source 206 (BBS) and photodetector (PD) 207 are coupled together by coupler 211. Since a single fiber 215 is used only as a light carrier while both the sample and reference arm are formed in free space inside the tube 201, the separate fibers (Fiber 1 and Fiber 2) for the reference and sample arm required by the conventional OCT probe 100 shown in FIG. 1 are not needed. The reference arm in probe 210 is embedded into the imaging probe as shown in FIG. 2(*b*), so that OCT imaging probe 210 has both the sample arm and the reference arm packaged inside the same small diameter tube 201. Since both sample and reference arm optical paths share the same optical fiber 215, fiber length mismatching and dispersion mismatching characteristic of conventional OCT systems are completely eliminated.

As noted above, a preferred enabling device for probes according to the invention is the large-vertical-displacement (LVD) MEMS mirror disclosed in U.S. Pat. No. 6,940,630. Briefly, the minor plate of the LVD micromirror moves out-of-plane up to 5 mm for the axial scanning and most importantly the footprint of the LVD micromirror is only about 2 to 5 mm.

A LVD Hybrid Micromirror can be used to generate the large vertical motions provided by the LVD mirror disclosed in application Ser. No. 10/835,344, and also add simultaneously oscillation at high frequency, >1 kHz and preferably >15 kHz, to provide phase modulation. The "hybrid" refers to the integration of electrothermal actuation for large vertical displacement and small-amplitude electrostatic actuation for high speed. Briefly, the mirror plate of the LVD micromirror moves out-of-plane up to 5 mm for the axial scanning and simultaneously oscillates at high frequency (>15 kHz) for phase modulation.

A cross sectional view of a single fiber OCT probe according to the invention is shown in FIG. 2(*b*). A broadband light source (not shown) is coupled into a single-mode optical fiber 215 which is coupled to an angled graded-index (GRIN) lens 218 and thereafter is collimated. Then two light beams are formed through a non-polarizing beam splitter (BS) 219, such as a BS cube (1 mm×1 mm×1 mm). The reference light beam is deflected to a LVD MEMS mirror or LVD hybrid MEMS mirror 225, while the light beam in the sample arm is guided to the sample by MEMS mirror 220. The light reflected off the LVD micromirror 225 and the light scattered from the sample tissue are coupled back to the beam splitter (BS) through fiber 215 to the photodetector (PD) 207. The interference signal is thus picked up by the photodetector (PD) 207.

One application of the single-fiber OCT probe 200 is to realize miniature full-field OCT probes. Since both the reference and sample arm are embedded inside the same imaging probe as shown in FIG. 2(*b*), a free-space interferometer is obtained.

Figure 3:
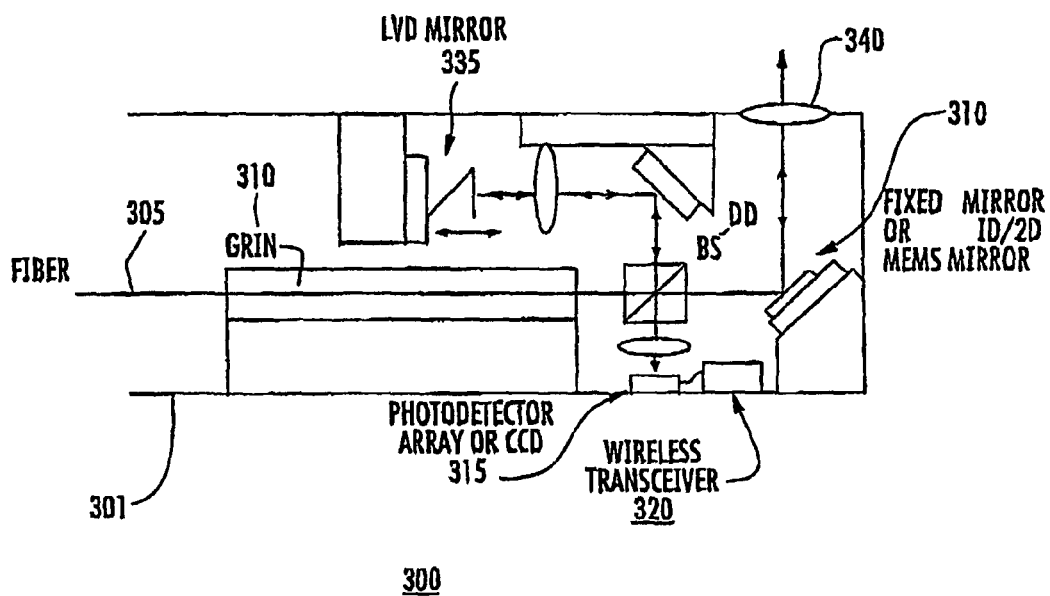
FIG. 3 shows a cross sectional view of a full-field endoscopic OCT imaging probe according to an embodiment of the invention that includes a LVD micromirror in the reference arm, and a photodetector array and wireless transceiver for wireless data transmission and control.

FIG. 3 shows a cross sectional view of a single-fiber full-field (SF$^3$) OCT imaging probe 300 that includes an additional mirror 310 in the sample arm for side view scanning embodied as a Linnick-type interferometer. All components shown are disposed in tube 301. The added mirror can be a fixed mirror, or a 1D or 2D MEMS scanning mirror to increase the lateral scanning range. Using a 2D MEMS scanning mirror for mirror 310, 3D OCT imaging can be provided. An array of photodetectors or CCD array 315 and a wireless transmitter 320 are disposed inside the imaging probe. A power source (e.g., battery, microwave or laser) may be also disposed inside the imaging probe (not shown).

Probe 300 is now described assuming a 2D MEMS scanning mirror is provided in the sample arm. A broadband light source (not shown) is coupled into an optical fiber. The light beam is delivered via the fiber 305 to an angled graded-index (GRIN) lens 310 and thereafter is collimated. Then two light beams are formed through a non-polarizing beam splitter (BS) 350, such as a BS cube (1 mm×1 mm×1 mm). The reference light beam is deflected to a large-vertical-displacement (LVD) MEMS mirror 335, while the light beam in the sample arm is guided to the 2D transversely scanning micromirror 310. The light reflected off the LVD micromirror 335 and the light scattered from the sample tissue and collected by a lens 340 are coupled back to the beam splitter 350 and then to the photodetector 315. Thus, the interference signal is picked up by the photodetector 315. En face scan scheme can be used, where the 2D micromirror 310 scans an x-y image at each vertical position of the axially scanning LVD micromirror 335, resulting in 3D images.

Figure 4:
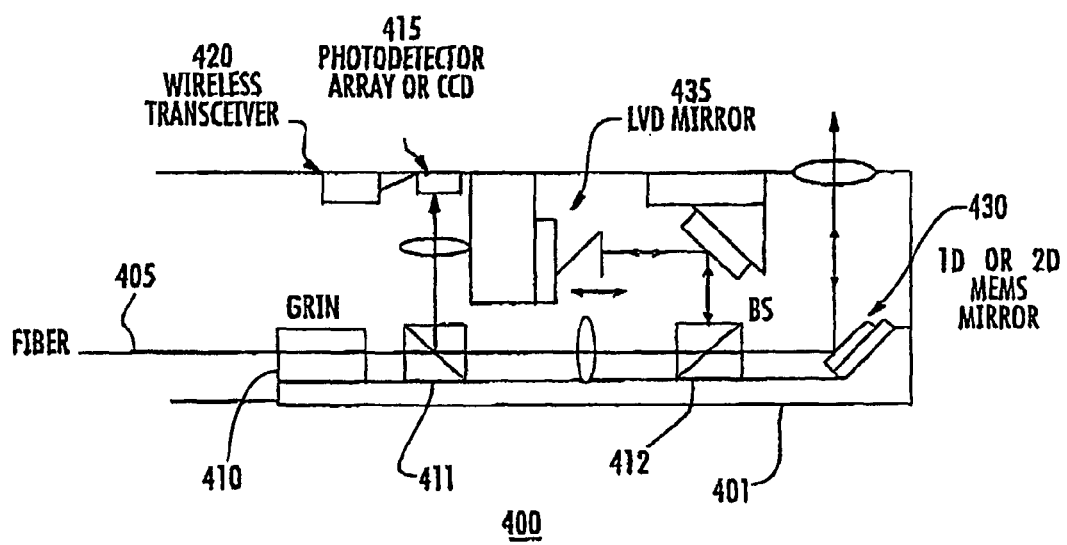
FIG. 4 shows a cross sectional view of a full-field endoscopic OCT imaging probe according to an embodiment of the invention that is a variation of the system shown in FIG. 3.

FIG. 4 shows the cross section of a single-fiber full-field (SF$^3$) OCT imaging probe 400 that includes a mirror in the sample arm 430 for side view scanning embodied as a Michelson-type interferometer. System components shown are disposed in tube 401 including single fiber 405, GRIN 410 and beam splitters 411 and 412. LVD mirror 435 provides axial scanning for the reference arm. An array of photodetectors 415 and a wireless transmitter 420 are disposed inside the imaging probe 400.

Figure 5:
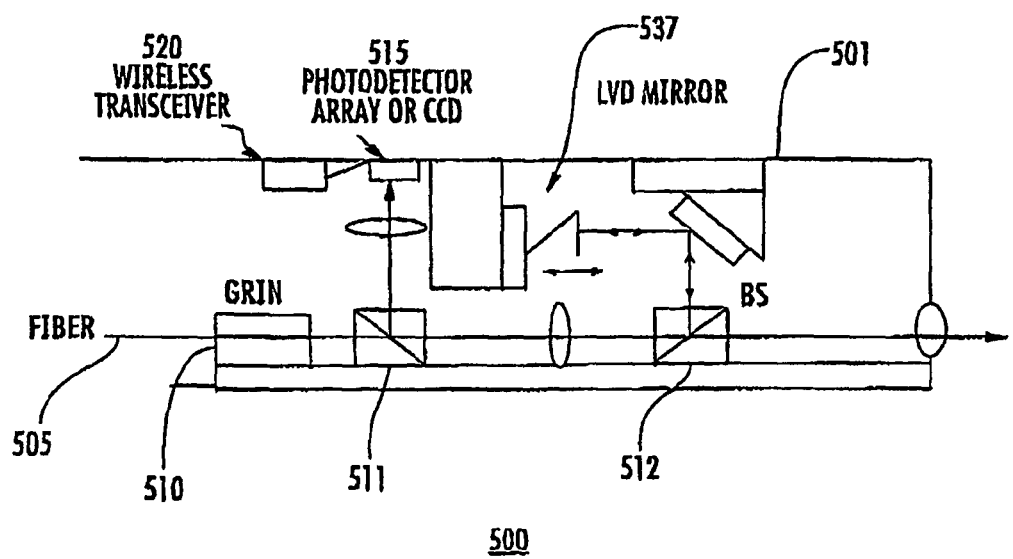
FIG. 5 shows a cross sectional view of a front-view full-field endoscopic OCT imaging probe according to an embodiment of the invention.

FIG. 5 shows the cross section of a single-fiber full-field (SF$^3$) OCT imaging probe 500 embodied as a Michelson-type interferometer for front view scanning. System components shown are disposed in tube 501 including single fiber 505, GRIN 510 and beam splitters 511 and 512. LVD mirror 535 provides axial scanning for the reference arm. An array of photodetectors 515 and a wireless transmitter 520 are disposed inside the imaging probe 500.

Figure 6:
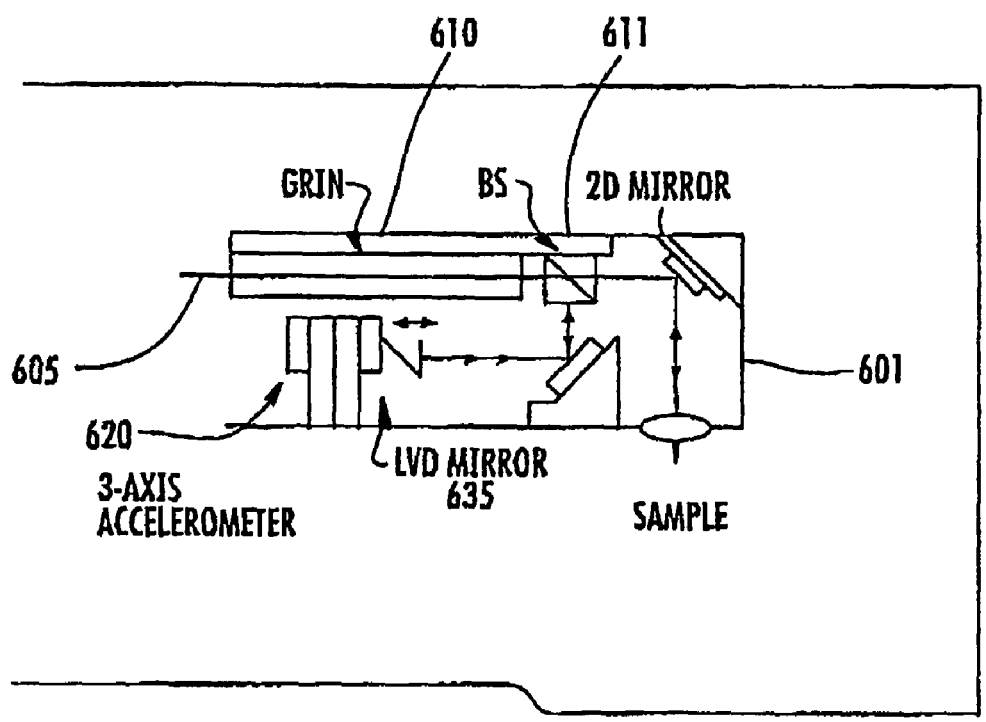
FIG. 6 shows a cross sectional view of a full-field OCT imaging probe according to an embodiment of the invention using a single optical fiber including a MEMS scanning mirror having a CMOS integrated 3-axis accelerometer inside the imaging probe for motion or vibration detection.

FIG. 6 shows the cross section of an OCT imaging probe 600 using a single optical fiber 610 including a MEMS scanning mirror having a CMOS integrated 3-axis accelerometer 620 on the same die inside the imaging probe 600 for motion or vibration detection. System components shown are disposed in tube 601 including single fiber 605, GRIN 610 and beam splitters 611. LVD mirror 635 provides axial scanning for the reference arm. A CMOS accelerometer 620 integrated with the MEMS mirror 635 monitors the motion of the imaging probe in real time, and thus provide fast 3D imaging with greatly reduced motion artifacts. Both the reference arm and sample arm are disposed entirely inside the probe 600. Although not shown, an array of photodetectors and a wireless transmitter analogous to the probe systems shown in FIGS. 2-5 can also be disposed inside the imaging probe.

Regarding the accelerometer integrated 2D micromirror, a curled-hinge vertical comb drive design is preferably used for large rotation angle and high speed. Meanwhile, an accelerometer can be integrated on the micromirror chip for position/vibration monitoring. The benefits that this MEMS device brings in include: 1) high speed, low power and large rotation angle, attributed to the electrostatic vertical comb drive; 2) 3D imaging due to the transverse x-y scanning of the 2D micromirror; 3) high-precision integrated angular position monitoring of the scanning mirror; and 4) in situ physiological activity real-time monitoring due to the integrated accelerometer.

Probes and related system according to the invention overcome, or at least substantially mitigate the following limitations present in conventional OCT or optical coherence microscopy (OCM) systems:

Size: For internal organ applications, miniature OCT imaging probes with diameters of a few millimeters must be developed. The invention overcomes this limitation. The new design will for the first time make it possible to make a compact full-field OCT/OCM imaging probe with only a few millimeters in diameter using MEMS devices which meet the size limitation.

Imaging speed: As noted above, most existing OCT systems perform image scanning of samples by moving an OCT probe or rotating the distal end of an optical fiber, which is slow and results in non-uniform optical coupling. The invention solves this problem by providing fast light beam scanning using MEMS mirrors, rather than through physical movement of the probe or fiber, making it ideally suited for clinical use of OCT systems.

Optical delay lines: Linear translating retroreflectors are dispersion-free and polarization-insensitive but bulky and slow. The Fourier domain rapid scanning optical delay line (RSOD) achieves several kHz scans, but it is complex and lossy and requires dispersion compensation. Using the LVD hybrid micromirror as linear translating retroreflectors can obtain high speed and significantly reduce the size.

Fiber length matching and Dispersion and polarization match in compensation: Even a small length mismatch between the fiber 1 and fiber 2 shown in FIG. 1 will cause dispersion that can significantly affect the axial resolution, and even if the fiber lengths are matched, the two fibers will experience different bending, twisting and temperature, which will induce dispersion and polarization mismatch. The invention overcomes both these limitations by utilizing a single fiber to deliver light, but no fibers in either the sample or reference arm.

In vivo intravascular or endoscopic full-field OCT imaging: In full-field OCT systems, a two-dimensional (2D) image is obtained for each axial scan without any lateral scan. So it is much faster. Moreover, high resolution can be obtained by using a large array of photodetectors, not limited by the light beam spot size. However, current full-field OCT systems are bulky and limited only to biopsy samples or for external use because of the requirement of forming a Michelson interferometer in free space with a bulky optical delay line.

The single-fiber full-field OCT-probe based systems according to the invention being highly compact can thus provide in vivo intravascular or endoscopic full-field OCT imaging. For example, the invention can be used for in vivo endoscopic and intravascular applications such as early cancer detection in visceral organs such as lung, bladder, gastrointestinal tracts and pancreas, and cardiovascular imaging, not possible using previously disclosed OCT probe-based systems.

An exemplary method for assembling OCT Probes according to the invention is now presented. Other suitable methods will be apparent to those having ordinary skill in the art. The catheter diameter of a prototype probe can be 6 mm, which is the outer diameter of most currently produced bronchoscopes. The catheter diameter can be further reduced to 2.8 mm or less so that it can be directly installed into the working channel of an adult endoscope (e.g., bronchoscope) to minimize the cost of instrument development for clinical use.

Figure 7:
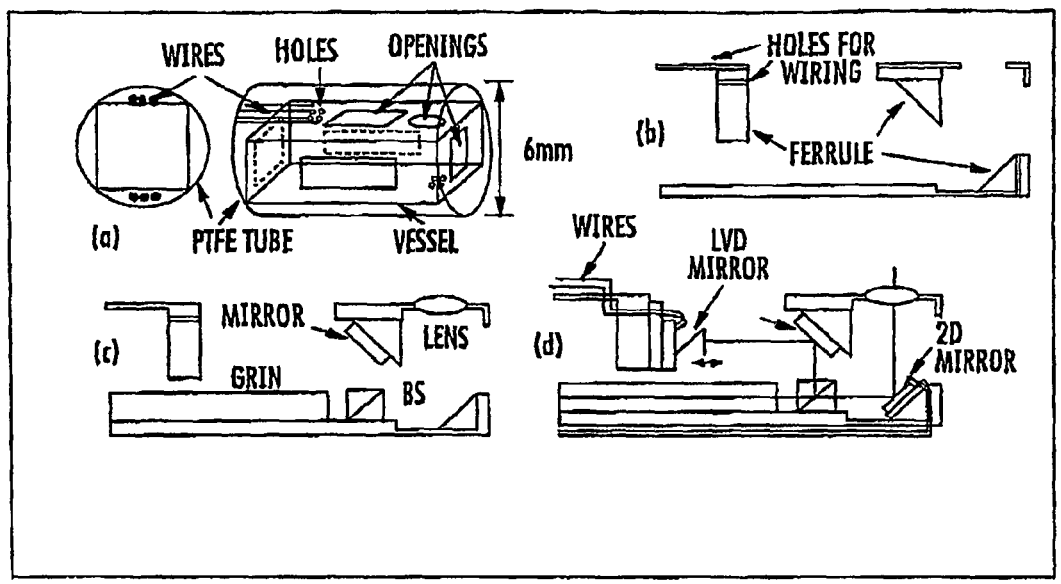
FIG. 7(a)-(d) shows an exemplary sequence for OCT probe packaging; 7(a) is an end view and side view; 7(b)-(d): a cross-sectional view (along the tube); 7(b) pre-machined holder, 7(c) installation of optical components, and 7(d) installation of MEMS devices.

One possible packaging method for the single-fiber OCT probes according to the invention is to install all micro-optical components into a rectangular vessel that is then encapsulated by a flexible biocompatible tube, as shown in FIG. 7(a). The vessel has openings for assembling optical components and MEMS devices. The electrical wires will run through the gaps between the vessel and the tube (FIG. 7(a)). The packaging starts with a steel frame or a plastic mold with custom high-precision machining (FIG. 7(b)). Then, the optical components including a spherical lens, beamsplitter and a graded-index (GRIN) lens can be installed (FIG. 7(c)). After that, the packaged LVD hybrid micromirror and 1D or 2D MEMS micromirror are assembled into the vessel (FIG. 7(d)). Finally, the loaded vessel is slipped into a biocompatible polymer, such as a polytetrafluoroethylene (PTFE) tube (FIG. 7(a)). PTFE is biocompatible, flexible and transparent to near-IR light.

This invention can be embodied in other forms without departing from the spirit or essential attributes thereof and, accordingly, reference should be had to the following claims rather than the foregoing specification as indicating the scope of the invention.

The invention claimed is:

1. A single fiber full-field optical coherence tomography (OCT) imaging probe, comprising:
   a hollow tube, and
   a single fiber disposed within said tube for transmitting light received from a broadband light source to a beam splitter in said tube optically coupled to said single fiber, said beam splitter splitting said light into a first and a second optical beam, wherein said first beam is optically coupled to a reference arm including a MEMS reference micromirror which provides axial scanning and said second beam is optically coupled to a sample arm for probing a sample to be imaged, wherein said reference arm and said sample arm both disposed in said tube.

2. The probe of claim 1, further comprising a photodetector array disposed inside said tube optically coupled to said beam splitter, said photodetector array receiving a reflected beam from said MEMS reference micromirror and a scattered beam from said sample to form an image of said sample.

3. The probe of claim 1, wherein said MEMS reference micromirror comprises a large vertical displacement (LVD) MEMS micromirror.

4. The probe of claim 3, wherein said LVD micromirror comprises an electrothermal bimorph actuator, a rigid frame and a mirror plate, wherein said LVD micromirror generates vertical motion.

5. The probe of claim 2, further comprising a wireless transceiver disposed inside said tube communicably coupled to said photodetector, said transceiver transmitting image data obtained from said photodetector over the air.

6. The probe of claim 1, further comprising a mirror disposed in said sample arm, wherein said mirror directs said second beam to a side of said tube for side-view scanning of said sample.

7. The probe of claim 6, wherein said mirror is a MEMS scanning mirror.

8. The probe of claim 3, wherein said LVD micromirror includes an integrated accelerometer on the same die.

9. The probe of claim 8, wherein said accelerometer is a three-axis accelerometer.

10. An optical coherence tomographic (OCT) probe-based imaging system for viewing a sample, comprising:
    said probe recited in claim 2, and
    a control module including at least one broadband light source for coupling said broadband light into said single fiber, and signal processing and synchronization electronics for coordinating, detecting and processing optical interference resulting from a scattered beam from said sample and a reflected beam from said reference arm both received via said single fiber.

11. The system of claim 10, further comprising a wireless transceiver disposed inside said tube communicably coupled to said photodetector, said transceiver transmitting image data over the air obtained from said photodetector.

* * * * *